US007205107B2

(12) United States Patent
Baugh et al.

(10) Patent No.: US 7,205,107 B2
(45) Date of Patent: Apr. 17, 2007

(54) MACROPHAGE MIGRATION INHIBITORY FACTOR (MIF) PROMOTER POLYMORPHISM IN INFLAMMATORY DISEASE

(75) Inventors: John A. Baugh, Kilpedder (IE); Richard Bucala, Cos Cob, CT (US); Smita Chitnis, San Diego, CA (US); Seamus C. Donnelly, Dublin (IE); Peter K. Gregersen, Larchmont, NY (US); Joanita Monteiro, Philadelphia, PA (US)

(73) Assignee: Cytokine Pharmasciences, Inc., King of Prussia, PA (US)

( * ) Notice: Subject to any disclaimer, the term of this patent is extended or adjusted under 35 U.S.C. 154(b) by 300 days.

(21) Appl. No.: 10/323,656

(22) Filed: Dec. 20, 2002

(65) Prior Publication Data

US 2003/0215446 A1 Nov. 20, 2003

Related U.S. Application Data

(60) Provisional application No. 60/341,832, filed on Dec. 21, 2001.

(51) Int. Cl.
*C12Q 1/68* (2006.01)
*C12P 19/34* (2006.01)
*C07H 21/04* (2006.01)
*C07H 21/02* (2006.01)
*A01N 37/18* (2006.01)
*A61K 38/00* (2006.01)

(52) U.S. Cl. .......................................... 435/6; 435/91.2
(58) Field of Classification Search ..................... None
See application file for complete search history.

(56) References Cited

U.S. PATENT DOCUMENTS 6,030,615 A 2/2000 Bucala et al.

OTHER PUBLICATIONS

Donn et al; Arthritis and Rheumatism, vol. 44, pp. 1782-1785; Aug. 2001.*
Barton et al; Genes and Immunity, vol. 4, pp. 487-491.*
Gregersen and Bucala, Arthritis and Rheumatism, vol. 48, pp. 1171-1176.*
Paralker et al; Genomics, vol. 19, pp. 48-51, 1994.*
Buck et al; Biotechniques, 1999 27:528-536.*
Ye et al; Nucleic Acids Research, vol. 22, pp. 5672-5678, 1994.*
J.A. Baugh, et al., "A Functional Promoter Polymorphism in the Macrophage Migration Inhibitory Factor (MIF) Gene Associated with Disease Severity in Rheumatoid Arthritis", Genes and Immunity, vol. 3, No. 3, May 2002.
Bucala, R., "MIF Rediscovered: Cytokine, Pituitary Hormone, and Glucocorticoid-Induced Regulator of the Immune Response", FASEB Journal, 10, 1607-1612 (1996).

Leech, M., et al., "Macrophage Migration Inhibitory Factor in Rheumatoid Arthritis", Arthritis & Rheumatism, vol. 42, No. 8, 1601-1608 (1999).
Bernhagen, J., et al., "MIF is a Pituitary-Derived Cytokine That Potentiates Lethal Endotoxaemia", Nature, vol. 365, 756-759 (1993).
Bernhagen, J., et al., "The Emerging Role of MIF in Septic Shock and Infection", Biotherapy, 8, 123-127 (1995).
Donnelly, S.C., et al., "Macrophage Migration Inhibitory Factor and Acute Lung Injury", Chest, 116:111S (Jul. 1999).
Yang, N., et al., "Reversal of Established Rat Crescentic Glomerulonephritis by Blockade of Macrophage Migration Inhibitory Factor (MIF): Potential Role of MIF in Regulating Glucocorticoid Production", Molecular Medicine, 4, 413-424 (1998).
David, J.R., "Delayed Hypersensitivity In Vitro: Its Mediation by Cell-Free Substances Formed by Lymphoid Cell-Antigen Interaction", Pathology, vol. 56, 72-77 (1966).
Calandra T., et al., "The Macrophage Is an Important and Previously Unrecognized Source of Macrophage Migration Inhibitory Factor", J. Exp. Med., vol. 179, 1895-1902 (1994).
Onodera, S., et al., "High Expression of Macrophage Migration Inhibitory Factor in the Synovial Tissues of Rheumatoid Joints", Cytokine, vol. 11, No. 2, 163-167 (1999).
Calandra, T., et al., "Protection From Septic Shock by Neutralization of Macrophage Migration Inhibitory Factor", Nature Medicine, vol. 6, No. 2, 164-170 (2000).
Bacher, M., et al., "An Essential Regulatory Role For Macrophage Migration Inhibitory Factor in T-cell Activation", Proc. Natl. Acad. Sci. USA, Immunology, vol. 93, 7849-7854 (1996).
Satoskar, A.R., et al., "Migration-Inhibitory Factor Gene-Deficient Mice Are Susceptible to Cutaneous *Leishmania major* Infection", Infection and Immunity, vol. 69, No. 2, 906-911 (2001).
Benigni, F., et al., "The Proinflammatory Mediator Macrophage Migration Inhibitory Factor Induces Glucose Catabolism in Muscle", Journal of Clin. Invest., vol. 106, No. 10, 1291-1300 (2000).
Abe, R., et al., "Regulation of the CTL Response by Macrophage Migration Inhibitory Factor", The Journal of Immunology, vol. 166, 747-753 (2001).

(Continued)

*Primary Examiner*—Jehanne Sitton
(74) *Attorney, Agent, or Firm*—Merchant & Gould, P.C.; Steven B. Kelber

(57) ABSTRACT

Describe herein is a CATT-tetranucleotide repeat polymorphism at position −817 of the human Mif gene that functionally affects the activity of the Macrophage Inhibitory Factor (MIF) promoter in gene reporter assays. Four genotypes are described which comprise 5, 6, 7, or 8-CATT repeat units. Of these, the 5-CATT allele has the lowest level of basal and stimulated MIF promoter activity in vitro. The presence of the low expressing, 5-CATT repeat allele correlated with low disease severity in a cohort of rheumatoid arthritis patients. Methods, compositions and apparatus for detecting this CATT-tetranucleotide repeat polymorphism at position −817 of the human Mif gene, and for using same for assessing predisposition to severe inflammatory disease, are also disclosed.

3 Claims, 5 Drawing Sheets

OTHER PUBLICATIONS

Bernhagen, J., et al., "Purification and Characterization of the Cytokine Macrophage Migration Inhibitory Factor (MIF)", Hormones, Mediators, 922, p. A1417.

Onodera, S., et al., "Macrophage Migration Inhibitory Factor Up-regulates Expression of Matrix Metalloproteinases in Synovial Fibroblasts of Rheumatoid Arthritis", The Journal of Biological Chemistry, vol. 275, No. 1, 444-450 (2000).

Meyer-Siegler, K., "Macrophage Migration Inhibitory Factor Increases MMP-2 Activity in DU-145 Prostate Cells", Cytokine, vol. 12, No. 7, 914-921 (2000).

Mitchell, R.A., et al., "Sustained Mitogen-activated Protein Kinase (MAPK) and Cytoplasmic Phospholipase A2 Activation by Macrophage Migration Inhibitory Factor (MIF)", The Journal of Biological Chemistry, vol. 274, No. 25, 18100-18106 (1999).

Hudson, J.D., et al., "A Proinflammatory Cytokine Inhibits p53 Tumor Suppressor Activity" J. Exp. Med., vol. 190, No. 10, 1375-1382 (1999).

Mitchell, R.A., et al., "Macrophage Migration Inhibitory Factor (MIF) Sustains Macrophage Proinflammatory Function by Inhibiting p53: Regulatory Role in the Innate Immune Response", PNAS, vol. 99, No. 1, 345-350 (2002).

Alam, J., et al., Reporter Genes: Application to the Study of Mammalian Gene Transcription, Analytical Biochemistry, 188, 245-254 (1990).

Naylor, L. H., "Reporter Gene Technology: The Future Looks Bright", Biochemical Pharmacology, vol. 58, 749-757 (1999).

Seamon, K.B., et al., "Forskolin: A Unique Diterpene Activator of Cyclic Amp-Generating Systems", Journal of Cyclic Nucleotide Research, 7, 4, 201-224 (1981).

McGuire, W., et al., "Variation in the TNF-α Promoter Region Associated With Susceptibility to Cerebral Malaria", Nature, vol. 371, 508-510 (1994).

Francis, S.E., et al., "Interleukin-1 Receptor Antagonist Gene Polymorphism and Coronary Artery Disease", Circulation, 99, 861-866 (1999).

Buchs, N., et al., "IL-1B and IL-1Ra Gene Polymorphisms and Disease Severity in Rheumatoid Arthritis: Interaction With Their Plasma Levels", Genes and Immunity, 2, 222-228 (2001).

Mu, H., et al., "Tumor Necrosis Factor a Microsatellite Polymorphism is Associated With Rheumatoid Arthritis Severity Through an Interaction With the HLA-DRB1 Shared Epitope", Arthritis & Rheumatism, vol. 42, No. 3, 438-442 (1999).

van Krugten, M.V., et al., "Association of the TNF +489 Polymorphism With Susceptibility and Radiographic Damage in Rheumatoid Arthritis", Genes and Immunity, 1, 91-96 (1999).

Sampey, A.V., et al., "Regulation of Synoviocyte Phospholipase $A_2$ Cyclooxygenase 2 by Macrophage Migration Inhibitory Factor", Arthritis & Rheumatism, vol. 44, No. 6, 1273-1280 (2001).

Mikulowska, A., et al., "Macrophage Migration Inhibitory Factor is Involved in the Pathogenesis of Collagen Type II-Induced Arthritis in Mice", The Journal of Immunology, 158, 5514-5517 (1997).

Leech, M., et al., "Regulation of Macrophage Migration Inhibitory Factor by Endogenous Glucocorticoids in Rat Adjuvant-Induced Arthritis", Arthritis & Rheumatism, vol. 43, No. 4, 827-833 (2000).

Nimer, S., et al., "The Repeated Sequence CATT(A/T) is Required for Granulocyte-Macrophage Colony-Stimulating Factor Promoter Activity", Molecular and Cellular Biology, vol. 10, No. 11, 6084-6088 (1990).

Nimer, S.D., et al., "Adjacent, Cooperative Elements Form a Strong, Constitutive Enhancer in the Human Granulocyte-Macrophage Colony-Stimulating Factor Gene", Blood, vol. 87, No. 9, 3694-3703 (1996).

Ye, J., et al., "Identification of a DNA Binding Site for the Nuclear Factor YY1 in the Human GM-CSF Core Promoter", Nucleic Acids Research, vol. 22, No. 25, (1994).

Ye, J., et al., "Characterization of the Human Granulocyte-Macrophage Colony-Stimulating Factor Gene Promoter: an AP1 Complex and an Sp1-Related Complex Transactive the Promoter Activity That is Suppressed by a YY1 Complex", Molecular and Cellular Biology, vol. 16, No. 1, 157-167 (1996).

Cohen, L.E., et al., "Role of Pit-1 in the Gene Expression of Growth Hormone, Prolactin, and Thyrotropin", Growth and Growth Disorders, vol. 25, No. 3, 523-540 (1996).

Calandra, T., et al., "MIF as a Glucocorticoid-Induced Modulator of Cytokine Production", Nature, vol. 377, 68-71 (1995).

Waeber, G., et al., "Transcriptional Activation of the Macrophage Migration-Inhibitory Factor Gene by the Corticotropin-Releasing Factor is Mediated by the Cyclic Adenosine 3',5'-Monophosphate Responsive Element-Binding Protein CREB in Pituitary Cells", Molecular Endocrinology, 12, 698-705 (1998).

Baerwald, C.G.O., et al., "Corticotropin Releasing Hormone (CRH) Promoter Polymorphisms in Various Ethnic Group of Patients with Rheumatoid Arthritis", Z Rheumatol., 59, 29-34 (2000).

Chikanza, I.C., et al., "Defective Hypothalamic Response to Immune and Inflammatory Stimuli in Patients with Rheumatoid Arthritis", Arthritis and Rheumatism, vol. 35, No. 11, 1281-1288 (1992).

Donn, R.P., et al., "A Novel 5'-Flanking Region Polymorphism of Macrophage Migration Inhibitory Factor is Associated With Systemic Onset Juvenile Idiopathic Arthritis", Arthritis & Rheumatism, vol. 44, No. 8, 1782-1785 (2001).

Feldmann, M., et al., "Anti-TNFα Therapy of Rheumatoid Arthritis: What Have We Learned?", Annu. Rev. Immunol., 19, 163-196 (2001).

Calandra, T., et al., "MIF, A Previously Unrecognized Macrophage Cytokine, Induces Macrophages to Secrete TNFα and Overomes Dexamethasone-Suppression of TNF Secretion", Clinical Research, vol. 42, No. 2, 138A (1994).

Paralkar, V., et al., "Cloning the Human Gene for Macrophage Migration Inhibitory Factor (MIF)", Genomics, 19, 48-51 (1994).

Tsuda, T., et al., "Separation of Nucleotides by High-Voltage Capillary Electrophoresis", Journal of Applied Biochemistry, 5, 330-336 (1983).

\* cited by examiner

FIG. 4A ctgcaggaac caataccat aggctatttg tataaatggg ccatggggcc tcccagctgg aggctggctg gtgccacgag ggtcccacag gcatgggtgt ccttcctata tcacatggcc ttcactgaga ctggtatatg gattgcacct atcagagacc aaggacagga cctccctgga aatctctgag gacctggcct gtgatccagt tgctgccttg tcctcttcct gctatgtcat

-817 ggcttatctt ctttcaccta↓ ttcattcatt cattcattca ttcagcagta ttagtcaatg tctcttgata tgcctggcac ctgctagatg gtccccgagt ttaccattag tggaaaagac atttaagaaa ttcaccaagg gctctatgag aggccataca cggtggacct gactagggtg tggcttccct gaggagctga agttgcccag aggcccagag aaggggagct gagcacgttt gaaccactga acctgctctg gacctcgcct ccttccttcg gtgcctccca gcatcctatc ctctttaaag agcaggggtt cagggaagtt ccctggatgg tgattcgcag gggcagctcc cctctcacct gccgcatgac taccccgccc catctcaaac acacaagctc acgcatgcgg gactggagcc cttgaggaca tgtggcccaa agacaggagg tacaggggct cagtgcgtgc agtggaatga actgggcttc atctctggaa gggtaagggg ccatcttccg ggttcaccgc cgcatcccca ccccggcac agcgcctcct ggcgactaac atcggtgact tagtgaaagg actaagaaag acccgaggcg aggccggaac aggccgattt ctagccgcca agtggagaac aggttggagc ggtgcgccgg gcttagcggc ggttgctgga ggaacgggcg gagtcgccca gggtcctgcc ctgcgggggt cgagccgagg caggcggtga cttccccact cggggcggag

+1 ccgcagcctc gcgggggcgg ggcctggcgc cggcggtggc gtcacaaaag gcgggaccac↓ agtggtgtcc gagaagtcag gcacgtagct cagcggcggc cgcggcgcgt gcgtctgtgc ctctgcgcgg gtctcctggt ccttctgcca tcatgccgat gttcatcgta aacaccaacg tgccccgcgc ctccgtgccg gacgggttcc tctccgagct cacccagcag ctggcgcagg ccaccggcaa gcccccccag gtttgccggg aggggacagg aagagggggg tgcccaccgg

FIG. 4B acgaggggtt ccgcgctggg agctggggag gcgactcctg aacggagctg ggggcgggg cgggggagg acggtggctc gggcccgaag tggacgttcg gggcccgacg aggtcgctgg ggcgggctga ccgcgcccu tcctcgcagt acatcgcggt gcacgtggtc ccggaccagc tcatggcctt cggcggctcc agcgagccgt gcgcgctctg cagcctgcac agcatcggca agatcggcgg cgcgcagaac cgctcctaca gcaagctgct gtgcggcctg ctggccgagc gcctgcgcat cagcccggac aggtacgcgg agtcgcggag gggcggggga ggggcggcgg cgcgcggcca ggcccgggac tgagccaccc gctgagtccg gcctcctccc cccgcagggt ctacatcaac tattacgaca tgaacgcggc caatgtgggc tggaacaact ccaccttcgc ctaagagccg cagggaccca cgctgtctgc gctggctcca cccgggaacc cgccgcacgc tgtgttctag gcccgcccac cccaaccttc tggtggggag aaataaacgg tttagagact aggagtgcct cggggttcct tggcttgcgg gaggaattgg tgcagagccg ggacattggg gagcgaggtc gggaaacggt gttgggggcg ggggtcaggg ccgggttgct ctcctcgaac ctgctgttcg ggagcccttt tgtccagcct gtccctccta cgctcctaac agaggagccc cagtgtcttt ccattctatg gcgtacgaag ggatgaggag aagttggcac tctgccctgg gctgcag

SEQUENCE LISTING

<160> NUMBER OF SEQ ID NOS: 12

<210> SEQ ID NO 1
<211> LENGTH: 22

```
<212> TYPE: DNA
<213> ORGANISM: Artificial Sequence
<220> FEATURE:
<223> OTHER INFORMATION: Primer

<400> SEQUENCE: 1
tgcaggaacc aatacccata gg                                              22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tgcgtgagct tgtgtgtttg ag                                              22

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
tcaaacacac aagctcacgc a                                               21

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
tggtcccgcc ttttgtg                                                    17

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5 cacaaaggc gggaccaca                                                   19

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
actgcgagga aagggcg                                                    17

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
```

```
cgccctttcc tcgcagt                                                          17
```

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8

```
tagaatggaa agacactggg                                                       20
```

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9

```
aatggtaaac tcggggag                                                         18
```

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10

```
ctcgagctgc aggaaccaat acccat                                                26
```

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11

```
aagcttggca tgatggcaga aggacc                                                26
```

<210> SEQ ID NO 12
<211> LENGTH: 2167
<212> TYPE: DNA
<213> ORGANISM: Homo sapiens

<400> SEQUENCE: 12

```
ctgcaggaac caatacccat aggctatttg tataaatggg ccatggggcc tcccagctgg           60
aggctggctg gtgccacgag ggtcccacag gcatgggtgt ccttcctata tcacatggcc          120
ttcactgaga ctggtatatg gattgcacct atcagagacc aaggacagga cctccctgga          180
aatctctgag gacctggcct gtgatccagt tgctgccttg tcctcttcct gctatgtcat          240
ggcttatctt cttttcaccca ttcattcatt cattcattca ttcagcagta ttagtcaatg         300
tctcttgata tgcctggcac ctgctagatg gtccccgagt ttaccattag tggaaaagac          360
atttaagaaa ttcaccaagg gctctatgag aggccataca cggtggacct gactagggtg          420
tggcttccct gaggagctga agttgcccag aggcccagag aaggggagct gagcacgttt          480
gaaccactga acctgctctg gacctcgcct ccttccttcg gtgcctccca gcatcctatc          540
ctctttaaag agcaggggtt cagggaagtt ccctggatgg tgattcgcag gggcagctcc          600
cctctcacct gccgcatgac tacccccgccc catctcaaac acacaagctc acgcatgcgg         660
```

```
                                                                -continued gactggagcc cttgaggaca tgtggcccaa agacaggagg tacaggggct cagtgcgtgc     720
agtggaatga actgggcttc atctctggaa gggtaagggg ccatcttccg ggttcaccgc     780
cgcatcccca cccccggcac agcgcctcct ggcgactaac atcggtgact tagtgaaagg     840
actaagaaag acccgaggcg aggccggaac aggccgattt ctagccgcca agtggagaac     900
aggttggagc ggtgcgccgg gcttagcggc ggttgctgga ggaacgggcg gagtcgccca     960
gggtcctgcc ctgcgggggt cgagccgagg caggcggtga cttccccact cggggcggag    1020
ccgcagcctc gcggggcgg ggcctggcgc cggcggtggc gtcacaaaag gcgggaccac     1080
agtggtgtcc gagaagtcag gcacgtagct cagcggcggc cgcggcgcgt gcgtctgtgc    1140
ctctgcgcgg gtctcctggt ccttctgcca tcatgccgat gttcatcgta aacaccaacg    1200
tgccccgcgc ctccgtgccg gacgggttcc tctccgagct cacccagcag ctggcgcagg    1260
ccaccggcaa gccccccag gtttgccggg aggggacagg aagagggggg tgcccaccgg     1320 acgagggggtt ccgcgctggg agctggggag gcgactcctg aacggagctg gggggcgggg   1380 cgggggagg acggtggctc gggcccgaag tggacgttcg gggcccgacg aggtcgctgg     1440
ggcgggctga ccgcgccctt tcctcgcagt acatcgcggt gcacgtggtc ccggaccagc    1500
tcatggcctt cggcggctcc agcgagccgt gcgcgctctg cagcctgcac agcatcggca    1560
agatcggcgg cgcgcagaac cgctcctaca gcaagctgct gtgcggcctg ctggccgagc    1620
gcctgcgcat cagcccggac aggtacgcg agtcgcggag gggcgggggga ggggcggcgg    1680 cgcgcggcca ggcccgggac tgagccaccc gctgagtccg gcctcctccc cccgcagggt    1740
ctacatcaac tattacgaca tgaacgcggc caatgtgggc tggaacaact ccaccttcgc    1800
ctaagagccg cagggaccca cgctgtctgc gctggctcca cccgggaacc cgccgcacgc    1860
tgtgttctag gcccgcccac cccaaccttc tggtggggag aaataaacgg tttagagact    1920
aggagtgcct cggggttcct tggcttgcgg gaggaattgg tgcagagccg ggacattggg    1980
gagcgaggtc gggaaacggt gttgggggcg ggggtcaggg ccgggttgct ctcctcgaac    2040
ctgctgttcg ggagcccttt tgtccagcct gtccctccta cgctcctaac agaggagccc    2100
cagtgtcttt ccattctatg gcgtacgaag ggatgaggag aagttggcac tctgccctgg    2160
gctgcag                                                              2167
```

MACROPHAGE MIGRATION INHIBITORY FACTOR (MIF) PROMOTER POLYMORPHISM IN INFLAMMATORY DISEASE

This application claims priority from U.S. Provisional Application Ser. No. 60/341,832 filed Dec. 21, 2001. The entirety of that provisional application is incorporated herein by reference.

BACKGROUND OF THE INVENTION

1. Field of the Invention

This invention relates to diagnostic method and apparatus based upon a functional polymorphism in the promoter of a gene encoding macrophage migration inhibitory factor (MIF). More specifically, this invention relates to a method for diagnosis of pre-disposition to certain disease states, by screening for the presence of this promoter polymorphism. The invention also relates to apparatus for screening for the polymorphism, MIF genes containing the polymorphism and to a probe therefor.

2. Background of the Technology

A number of experimental studies have led to the concept that macrophage migration inhibitory factor (MIF) functions as a physiological counter-regulator of glucocorticoid action within the immune system. In this role, MIF's position within the cytokine cascade is to act in concert with endogenous glucocorticoids to control the set point and the magnitude of the inflammatory response (1). MIF also has several direct, pro-inflammatory roles in inflammatory diseases such as rheumatoid arthritis (2), sepsis (3, 4), acute respiratory distress syndrome (5), and glomerulonephritis (6).

MIF was originally described over 30 years ago as a T-lymphocyte-derived factor that inhibited the migration of peritoneal macrophages (7), but it is now known that several other cell types, including macrophages themselves, are important sources of MIF (8). MIF levels are elevated in the serum and synovial fluid of patients with rheumatoid arthritis (2, 9), and within the synovial joint MIF immunostaining can be localized to the synovial lining CD 14+ macrophages and fibroblast-like synoviocytes (2). Upon release MIF is directly pro-inflammatory by activating or promoting cytokine expression (TNF$\alpha$ (8, 10), IL-1$\beta$, IL-2 (11), IL-6 (8,12), IL-8 (13) and IFN$\gamma$ (11, 14)), nitric oxide release (15), matrix metalloproteinase (MMP) expression (16, 17), and induction of the cyclooxygenase-2 (Cox-2) pathway (18). MIF's capacity to induce to sustained activation of the p44/p42 (ERK-1/2) MAP kinase pathway (18) and to inhibit p53-dependent apoptosis (19, 20) also suggest that this mediator may play a key role in initiation of rheumatoid pannus.

U.S. Pat. No. 6,030,615 to Bucala, et al. discloses a combination method for treating diseases caused by cytokine-mediated toxicity, comprising administering an effective amount of (a) an MIF inhibitor, such as an antibody that binds to an MIF polypeptide, wherein the MIF polypeptide has a molecular weight of about 12.5 kDa in combination with (b) anti-TNF$\alpha$, anti-IL1, anti-IFN-$\gamma$, IL-1RA, a steroid, a glucocorticoid, or IL-10.

The concept that polymorphisms in immune response genes contribute to the pathogenesis of certain human autoimmune/inflammatory diseases has received increasing interest over the last several years. At present, very few gene polymorphisms have been shown to be functionally significant and to be of prognostic value in specific disease states. Previously defined examples include polymorphisms in TNF$\alpha$ and IL-1ra that have been shown to have certain prognostic significance in malaria and ischaemic heart disease respectively (24,25). Similarly, a number, of polymorphisms in TNF$\alpha$ and IL-$\beta$ have been reported to be associated with rheumatoid arthritis severity (26–28).

SUMMARY OF THE INVENTION

The present invention is based in part upon identification of a novel polymorphism in the human Mif gene that consists of a tetra-nucleotide CATT repeat located at position –817 of the Mif promoter. As disclosed herein, this promoter polymorphism is functionally significant in vitro, and analysis of a cohort of patients with rheumatoid arthritis indicates that this CATT repeat is associated with disease severity.

One object of this invention, therefore, is to provide a method of diagnosis comprising determining the genotype of a human Mif promoter.

Another object of this invention is to provide diagnostic means, comprising a means for determining the genotype of a human Mif promoter.

Accordingly, the invention relates to a method of diagnosis of severity of a non-infectious inflammatory disease or of a predisposition to severity of a non-infectious inflammatory disease comprising detecting a polymorphism in a human Mif promoter that correlates with an increase or decrease in MIF polypeptide expression. In this method the non-infectious inflammatory disease is, for instance, autoimmunity, graft versus host disease, or preferably rheumatoid arthritis, and preferably detection of the polymorphism is indicative of the severity of the disease or predisposition to severity of the disease. Preferably, this polymorphism in a human Mif promoter that correlates with an increase or decrease in MIF polypeptide expression is a CATT-tretra-nucleotide repeat polymorphism at position –817 of the human Mif gene, selected from the group consisting of 5, 6, 7 and 8 repeat units, where presence of the 5 repeat unit indicates occurrence of or predisposition to low disease severity.

The diagnostic method of of the invention preferably comprises a step of amplifying the Mif promoter using a PCR technique. For this purpose, the invention provides a PCR primer set selected to amplify a region of a human Mif promoter. For instance, the PCR primer set may be selected from the group consisting of: (i) MIF-F (–1024) and MIF-R (–421); (ii) MIF-F (–441) and MIF-R (+4); (iii) MIF-F (–13) and MIF-R (+395); and (iv) MIF-F (+379) and MIF-R (+1043), as shown in Table 1, infra. The invention also relates to a method of using a primer set of the invention to detect a polymorphism in a human Mif promoter region, and an article of manufacture (such as a diagnostic kit) comprising a PCR primer set of the invention.

The invention further relates to nucleic acid molecule comprising a human Mif promoter sequence in which the CATT-tetranucleotide at position –817 is repeated 5, 6, 7 or 8 times. Preferably, the nucleic acid molecule is an isolated DNA molecule, particularly an isolated genomic DNA fragment that has been amplified from a DNA sample of a human subject. In preferred embodiments, the isolated nucleic acid molecule of the invention comprises a portion of a human Mif promoter that comprises a CATT-tretra-nucleotide repeat polymorphism at position –817 of the human Mif gene.

Another aspect of the present invention relates to a method of inflammatory disease therapy comprising screening an individual for severity of a non-infectious inflammatory disease or of a predisposition to severity of a non-infectious inflammatory disease. This method comprises: detecting in a human subject a polymorphism in a human Mif promoter that correlates with an increase or decrease in MIF polypeptide expression, where detection of the polymorphism is indicative of the severity of the disease or predisposition to severity of the disease. This method of inflammatory disease therapy further comprises treating the human subject to prevent or reduce the severity of the inflammatory disease or to delay the onset of the inflammatory disease. For instance, the therapy may comprise treating the human subject by administering an effective amount of at least one agent selected from the group consisting of an MIF inhibitor, an anti-TNFα antibody, an anti-IL1 antibody, and anti-IFN-γ antibody, IL-1RA, a steroid, a glucocorticoid, and IL-10.

In a preferred embodiment of the invention method of inflammatory disease therapy the inflammatory disease is rheumatoid arthritis and the polymorphism in a human Mif promoter is a CATT-tretranucleotide repeat polymorphism at position −817 of the human Mif gene.

BRIEF DESCRIPTION OF THE FIGURES

FIGS. 4A and 4B depicts the nucleic acid sequence for human Mif (SEQ ID NO: 12). The nucleotide position designated as −817 in the figure is position 259 of SEQ ID NO: 12.

DETAILED DESCRIPTION OF THE INVENTION

Figure 1:
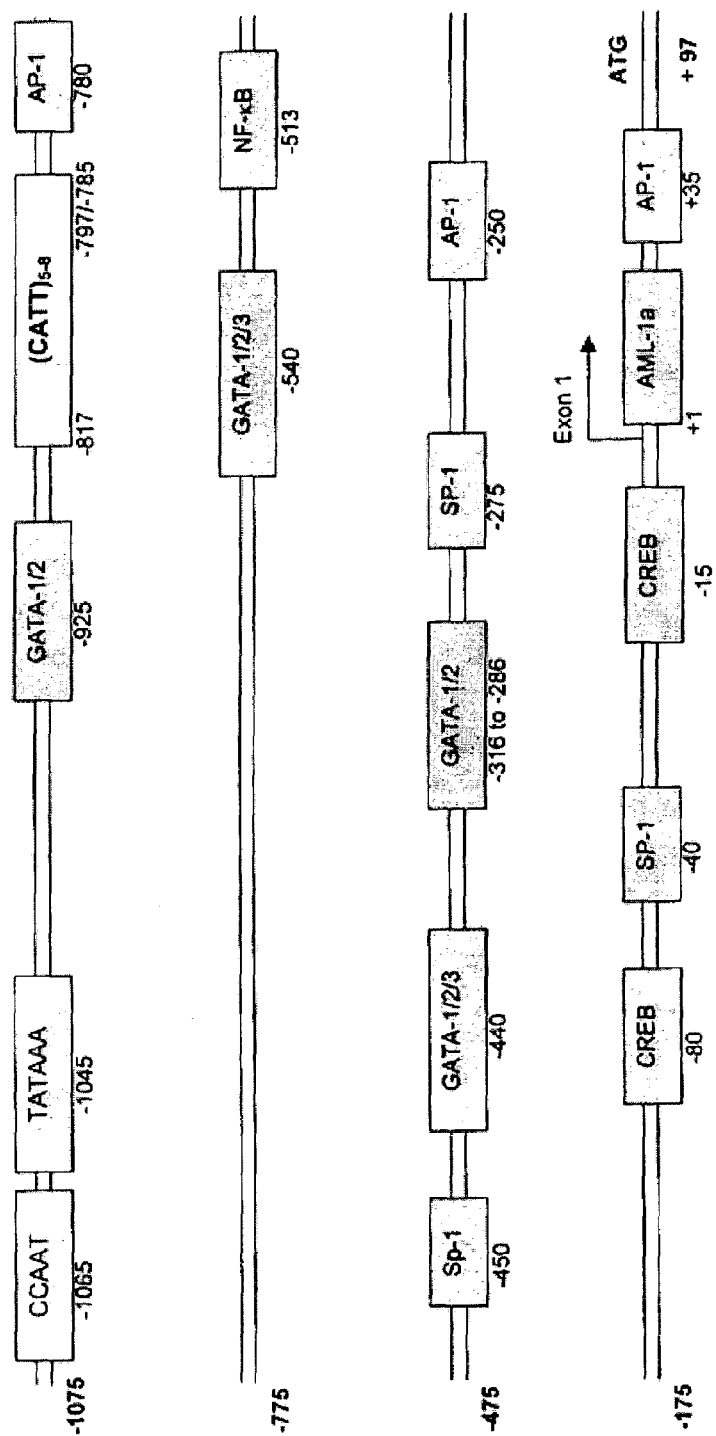
FIG. 1 shows a schematic representation of the human Mif promoter region. Putative transcription factor binding sites and areas of interest are boxed. The polymorphic CATT repeat region (−817 to −797/−785) is indicated by a lack of shading.

The novel Mif gene polymorphism identified herein is associated with reduced MIF promoter activity, and the presence of this genotype in the homozygous state appears to be associated with a reduced risk of severe rheumatoid arthritis.

MIF has been shown to promote TNFα secretion and to enhance IFNγ induced nitric oxide secretion from macrophages (8). In addition, MIF is an important autocrine regulator of macrophage (8), T-cell (11) and fibroblast activation (18). These data have led to numerous investigations of the potential role for MIF in chronic inflammatory conditions such as rheumatoid arthritis.

MIF protein levels circulate in higher levels in serum of rheumatoid arthritis patients and cellular MIF expression is enhanced within the synovium (2, 9). Cultured synovial fibroblasts obtained from patients with rheumatoid arthritis secrete significant quantities of MIF spontaneously in culture, and secretion increases further following pro-inflammatory stimulation (2). MIF stimulation of rheumatoid synovial fibroblasts results in increased expression of matrix metalloproteinases (16), as well as the induction of phospholipase $A_2$ ($PLA_2$) and COX-2 expression (29). Immunoneutralization of MIF activity in synoviocyte cultures also has been shown to inhibit IL-Iβ induced expression of COX-2 and $PLA_2$ mRNA (29). The administration of a neutralizing anti-MIF antibody also delays the onset and decreases the severity of type-II collagen induced arthritis in mice (30) and profoundly inhibits the development of adjuvant-induced arthritis in rats (31). Thus, there is considerable evidence implicating MIF in the pathogenesis of inflammatory arthritis.

Disclosed herein is a significant association between patients that are homozygous for the low expressing, 5-CATT allele and less aggressive rheumatoid disease. Only 1/79 (1.2%) patients with severe rheumatoid arthritis inherited this genotype, compared with 101105 (9.5%) of patients with milder, non-progressive disease. This suggests that a genetic predisposition to low expression of MIF protects against persistent inflammation and/or joint destruction. It is unknown at present which transcription factors may be involved in modulating the transcriptional effects of the polymorphic region, but the 5-CATT allele shows reduced responses in vitro to both serum and forskolin stimulation as well as reduced basal activity. A CATT repeated element also exists in the promoter of human granulocyte-macrophage colony-stimulating factor (GM-CSF), and is required for promoter activity (32, 33). It has been shown that the nuclear factor YY1[34], and more recently the factors AP-1 and SP-1, can form complexes with this region of the GM-CSF promoter (35). Whether any of these same factors also influence the activity of the MIF CATT repeat remains to be determined.

The CATT-repeat region within the Mif gene contains several putative Pit-1 transcription factor binding sites. Pit-1 is a pituitary-specific transcription factor that is critical for the expression of pituitary hormones such as prolactin and growth hormone (36). The anterior pituitary gland is an important source of MIF in rodents (3) and secretes MIF in response to physiological or infective stress (37). Corticotrophin-releasing factor (CRF) also has been shown to be a potent inducer of MIF expression in cultured pituitary cells. A recent functional analysis of the murine MIF gene-promoter using rat pituitary cells and the pituitary cell line AtT-20 demonstrated that CRF-induced gene expression is dependent upon a cAMP responsive element binding protein (38). Interestingly, reports of linkage of the CRF locus to rheumatoid arthritis have recently appeared in the literature, and there is some evidence that the hypothalamic pituitary—adrenal (HPA) axis may play a role in the pathogenesis of rheumatoid arthritis in certain patients. Patients with active rheumatoid arthritis have been shown to have abnormally low diurnal cortisol levels in the face of normal pituitary and adrenal function, suggesting a defect at the hypothalamic level (40). Given MIF's capacity to counter-regulate glucocorticoid action within the immune system (reviewed by Bucala (1)), the expression of MIF by the anterior pituitary gland may be important to the development of inflammatory diseases such as rheumatoid arthritis.

Since the initiation of these studies, a −173*G/C single nucleotide polymorphism (SNP) in the Mif gene promoter has been reported by Donn, et al. (41) and was shown to be associated with systemic-onset juvenile idiopathic arthritis (systemic-onset JIA). The possession of at least one 173*C allele was seen in 36.8% of patients with systemic-onset JIA compared to 20.3% of the normal population (41). However, there is no information concerning the effect of this SNP on gene expression. A preliminary analysis by the present inventors indicates that the 173*C allele cannot explain the present association data or results of promoter assays; indeed, there is no evidence of positive linkage disequilibrium between the 173*C allele and the 5-CAAT allele (data not shown).

TNFα is considered to be a critical effector cytokine in rheumatoid arthritis, and anti-TNFα therapy has emerged to have high efficacy in the treatment of this disease (42). Of note, there is a close relationship between MIF and TNFα. MIF appears to act as an important upstream regulator of TNFα expression. MIF promotes secretion of TNFα from macrophages and overrides the ability of glucocorticoids to suppress macrophage TNFα production (43). Immunoneutralization of MIF also reduces circulating levels of TNFα (3). In a clinical setting, the analysis of MIF polymorphisms provides a prognosticator of disease severity, particularly in inflammatory diseases and more particularly in rheumatoid disease, and can assist in the selection of interventional therapy. The data herein also reaffirm the potential importance of MIF as a therapeutic target in rheumatoid arthritis and possibly other inflammatory diseases.

Experimental

Materials and Methods

Patients: DNA samples were obtained from the Wichita Rheumatic Disease Data Bank and were representative of Caucasian patients followed in a rheumatology practice since 1974. The rheumatoid arthritis patients were divided into 2 groups using the following criteria: A) Severe (n=79); mean age at onset 55 years, mean disease duration of 13 years, mean Larsen score rate of 4.0, mean RF titer of 339.24 and a mean HAQ score.o.f 1.36. B) Mild (n=105); mean age at onset 45 years, mean disease duration of 15 years, mean Larsen score of 1.0, mean RF titer of 362.84 and a mean HAQ score of 0.93. Healthy Caucasian volunteers provided genomic DNA that was used as the normal control group (n=159).

DNA extraction: DNA was extracted from whole blood using the G Nome kit (Bio 101 Inc., CA, USA) and from the buccal brushes using the Pure Gene Kit® (Gentra Systems Inc., MN, USA).

Mif gene Sequencing and Polymorphism analysis: The Mif gene (GenBank Accession number: L19686, hereby incorporated in its entirety herein by reference) is located on chromosome 22q11.2 (44). The gene is 2167 bp long and has 3 exons separated by 2 introns of 189 bp and 95 bp. Four sets of primers were used to span the entire gene (Table 1, below).

TABLE 1

Primer sequences and conditions for PCR of the Mif Gene

| PCR Primer Set | Locations | Primer Sequences (5'-3') | Annealing Temp (° C.) | Special Conditions | PCR Product Size |
|---|---|---|---|---|---|
| SET 1 | MIF-F (−1074) MIF-R (−421) | TGCAGGAACCAATACCCATAGG (SEQ. ID NO:1) TGCGTGAGCTTGTGTGTTTGAG (SEQ. ID NO:2) | 58.1 | | 654 bp |
| SET 2 | MIF-F (−441) MIF-R (+4) | TCAAACACACAAGCTCACGCA (SEQ. ID NO:3) TGGTCCCGCCTTTTGTG (SEQ. ID NO:4) | 60.8 | 10% DMSO | 445 bp |
| SET 3 | MIF-F (−13) MIF-R (+395) | CACAAAAGGCGGGACCACA (SEQ. ID NO:5) ACTGCGAGGAAAGGGCG (SEQ. ID NO:6) | 62.3 | 25% 7-Deaza GTP in 1.25 mM dNTP | 408 bp |
| SET 4 | MIF-F (+379) MIF-R (+1043) | CGCCCTTTCCTCGCAGT (SEQ. ID NO:7) TAGAATGGAAAGACACTGGG (SEQ. ID NO:8) | | 10% DMSO | 665 bp |

The PCR reaction consisted of 1×PCR buffer II (Perkin Elmer, CA, USA), 20 ng DNA, 1.5 mM $MgCl_2$, 20 pmoles each of forward and reverse primers and 0.5 units of Amplitaq Gold® polymerase (Perkin Elmer—Applied Biosystems, CA, USA). The dNTP were used at a concentration of 0.2 mM except for set 3, where the 0.2 mM dNTP had 0.05 mM of 7-Deaza GTP in a 20 μl PCR reaction. The PCR conditions were as follows: 95° C./12 min, followed by 40 cycles of 95° C./30 sec, annealing temp (Table 1)/30 sec, 72° C./60 sec and 72° C./10 min. The PCR products were resolved using a 1% agarose gel stained with ethidium bromide.

The PCR products from 6 normal controls and 6 rheumatoid arthritis patients were sequenced using the Big Dye Terminator® cycle sequencing ready reaction kit (Perkin Elmer-Applied Biosystems). The sequences from all four primer sets were compiled to represent the entire Mif gene and were compared to analyze differences between the rheumatoid arthritis group and the normal controls.

Rapid screening for CATT repeat polymorphism: The forward primer from Set 1 (SEQ. ID. NO: 1) was used with the reverse primer MIF-R-728 (5'-AATGG-TAAACTCGGGGAC-3'; SEQ. ID NO: 9). The reverse primer was fluorescently labeled with TET to allow detection of the PCR products using capillary electrophoresis (45).

The PCR conditions were 1×PCR Buffer II, 1.5 mM MgCl$_2$, 0.2 mM dNTP, 0.75 pmoles of each primer, 1 ng DNA, 0.05 μl AmpliTaq Gold® polymerase in a 10 μl PCR reaction. The PCR cycling conditions used were the same as described above except for annealing conditions of 53.8° C./30 sec. 1 μl of diluted PCR product was added to 12 μl of deionized formamide containing 0.5 μl GS-500 TAMRA size standard (Perkin Elmer-Applied Biosystems). Samples were denatured before being resolved using an ABI 310 Genetic Analyzer (Perkin Elmer-Applied Biosystems). DNA samples from homozygous individuals that previously had been fully sequenced were used as controls for the repeat sizes obtained by capillary electrophoresis.

MIF Promoter cloning and Reporter Assays: Genomic DNA obtained from the primary screening that contained the 5, 6, 7, or 8-CATT tetranucleotide repeat polymorphism was used as a PCR template for initial cloning into the pCR2.1-TOPO vector (Invitrogen, CA, USA). The following primers were used to generate a 1173–1189 bp PCR product representing 1071–1087 bp of the upstream flanking region of the MIF coding sequence plus the first 102 bp of exon I (see FIG. 1):

```
Forward primer:
5'-CTCGAGCTGCAGGAACCAATACCCAT-3'    (SEQ. ID NO:10);

Reverse primer:
5'-AAGCTTGGCATGATGGCAGAAGGACC-3'    (SEQ. ID NO:12).
```

After complete sequencing, the promoter region was excised from the pCR2.1 vector and cloned into the XhoI/HindIII sites of the pGL3-Basic luciferase vector (Promega, Wis., USA). This vector contains the CDNA encoding a modified version of firefly luciferase in the absence of eukaryotic enhancer or promoter elements. Luciferase constructs directly regulated by the MIF promoter, containing the 5, 6, 7, or 8-CATT polymorphism, were generated. Transient transfections were carried out using 3 μl Fugene 6 (Roche, N.J., USA) and 1 μg of DNA per well of a six well plate as per manufacturers directions. Cell lines used included Cos-7 (monkey kidney fibroblast), A549 (human lung epithelium) and CCD-19LU (primary human lung fibroblast). Data were normalized in relation to an internal control of Renilla luciferase that was regulated by the Herpes simplex virus thymidine kinase promoter (PRL-TK vector—Promega, Wis., USA). Subsequently, each transfection consisted of 800 ng of test DNA (MIF-promoter regulated Luciferase gene) combined with 200 ng of PRL-TK control vector DNA. Luciferase assays were measured using a TD-20/20 luminometer (Turner Designs, Calif., USA) and the Dual Luciferase Reporter System (Promega, Wis., USA). Basal promoter activity was determined by measuring luciferase activity 36 hours after transfection. In some cases, cells were stimulated for the last 20 hours of culture prior to measurement of promoter activity.

Genotype and statistical analysis: The data were analyzed using Genotyper® 2.1 software (Perkin Elmer—Applied Biosystems, Calif., USA). The relationship between the genotypes and disease status (normal, mild or severe) was examined using the chi-square test and Fishers' exact test. Gene reporter assays were repeated 3 to 10 times in duplicate. Data are presented as mean±STDEV and compared by non-parametric Mann-Whitney U tests. Significance was defined as $P<0.05$.

Results

Identification of a Microsatellite Repeat in the Mif Promoter. Genomic DNA from six normal volunteers and six rheumatoid patients was utilized for full sequencing of the Mif gene. Due to the high GC content of this gene, the analysis was carried out in four sections. Alignment of all twelve sequences identified a tetra-nucleotide CATT repeat polymorphism in the upstream promoter region at position –817 (FIG. 1). Individuals having 5, 6, 7 or 8-CATT repeat alleles in their sequences were found. Individuals were either heterozygous or homozygous for these alleles, although no 7-CATT homozygotes were found in the normal population and no 8-CATT homozygotes were found in either population studied.

For rapid screening of the promoter polymorphism, a fluorescently labeled reverse primer that was proximal to the tetranucleotide repeat units was designed in order to amplify a smaller PCR fragment (340–352 bp). This fragment then was analyzed using capillary electrophoresis on an ABI 310 Genetic analyzer. The DNA of individuals previously sequenced was used as a template to generate control DNA fragments in order to correlate the fragment size observed on the ABI 310 analyzer with the number of CATT repeats in the test samples. Accordingly, the 4 PCR product sizes were 340, 344, 348, and 352 bp in length, and these corresponded to five, six, seven, and eight-CATT repeats, respectively. The genotypes observed were: 5,5; 5,6; 5,7; 6,6; 6,7; 7,7; 5,8; and 6,8. The 8,8 genotype was not seen in either the normal (n=159) or patient (n=184) populations; and the 7,7 genotype was not seen in the normal population, but was observed in one patient within the rheumatoid arthritis group.

Distribution of Mif Alleles in Normal Controls and Rheumatoid Arthritis Patients. The distribution of the different Mif alleles in normal controls, mild rheumatoid arthritis and severe rheumatoid arthritis patients are shown in Table 2, below.

TABLE 2

Distribution of MIF genotypes and the frequency of 5-CATT allele in normal and rheumatoid arthritis (RA) popluations.

| Population | MIF-Genotype | | | | | | | | Frequency of 5-CATT allele | |
|---|---|---|---|---|---|---|---|---|---|---|
| | 5,5 | 6,6 | 7,7 | 5,6 | 5,7 | 6,7 | 5,8 | 6,8 | 5,5 or 5,X alleles | X,X alleles |
| Normal (n = 159) | 8 (5.03%) | 53 (33.33%) | 0 | 61 (38.36%) | 10 (6.3%) | 25 (15.72%) | 1 (0.63%) | 1 (0.63%) | 80 (50.31%) | 79 (49.69%) |
| Wichita | 10 | 49 | 1 | 23 | 8 | 14 | 0 | 0 | 41 | 64 |

TABLE 2-continued

Distribution of MIF genotypes and the frequency of 5-CATT allele in normal and rheumatoid arthritis (RA) popluations.

| Population | MIF-Genotype | | | | | | | | Frequency of 5-CATT allele | |
|---|---|---|---|---|---|---|---|---|---|---|
| | 5,5 | 6,6 | 7,7 | 5,6 | 5,7 | 6,7 | 5,8 | 6,8 | 5,5 or 5,X alleles | X,X alleles |
| Mild RA (n = 105) | (9.52%) | (46.67%) | (0.95%) | (21.91%) | (7.62%) | (13.33%) | | | (39.05%) | (60.95%) |
| Wichita Severe RA (n = 79) | 1 (1.27%) | 40 (50.63%) | 0 | 20 (25.31%) | 4 (5.06%) | 13 (16.46%) | 0 | 1 (1.27%) | 25 (31.65%) | 54 (68.35%) |

There was no deviation from Hardy-Weinberg equilibrium in normal controls (p=0.69). The frequencies of the 5, 6, 7 and 8 alleles were found to be 0.277, 0.607, 0.11 and 0.006 respectively.

The number of individuals carrying at least one 5-CATT allele decreases from 50.31% in the normal population to 31.65% in the severe rheumatoid arthritis population (Table 2). The difference between the severe rheumatoid arthritis patients and controls is statistically significant (p<0.02). The cases and controls analyzed in this study were not closely matched for geographic and ethnic origin, hence the data must be interpreted with some caution. A comparison of specific genotypes between the mild and severe rheumatoid arthritis populations was therefore carried out, as shown in Table 2. The 5,5 genotype is observed in 9.5% of the patients with mild rheumatoid arthritis, but is significantly decreased to 1.3% in the patients with severe disease (p=0.0252 by Fisher's exact test). These data indicate that a homozygous 5-CATT allele is protective for the development of severe disease.

Effect of the CATT repeat polymorphism on MIF promoter activity. To investigate whether the CATT repeat polymorphism was associated with functional regulation of MIF expression, a gene reporter assay was developed and studied under defined conditions in vitro. Gene reporter assays have been widely employed to study transcriptional regulation, or as readouts to monitor transcription factor (21,22).

Figure 2:
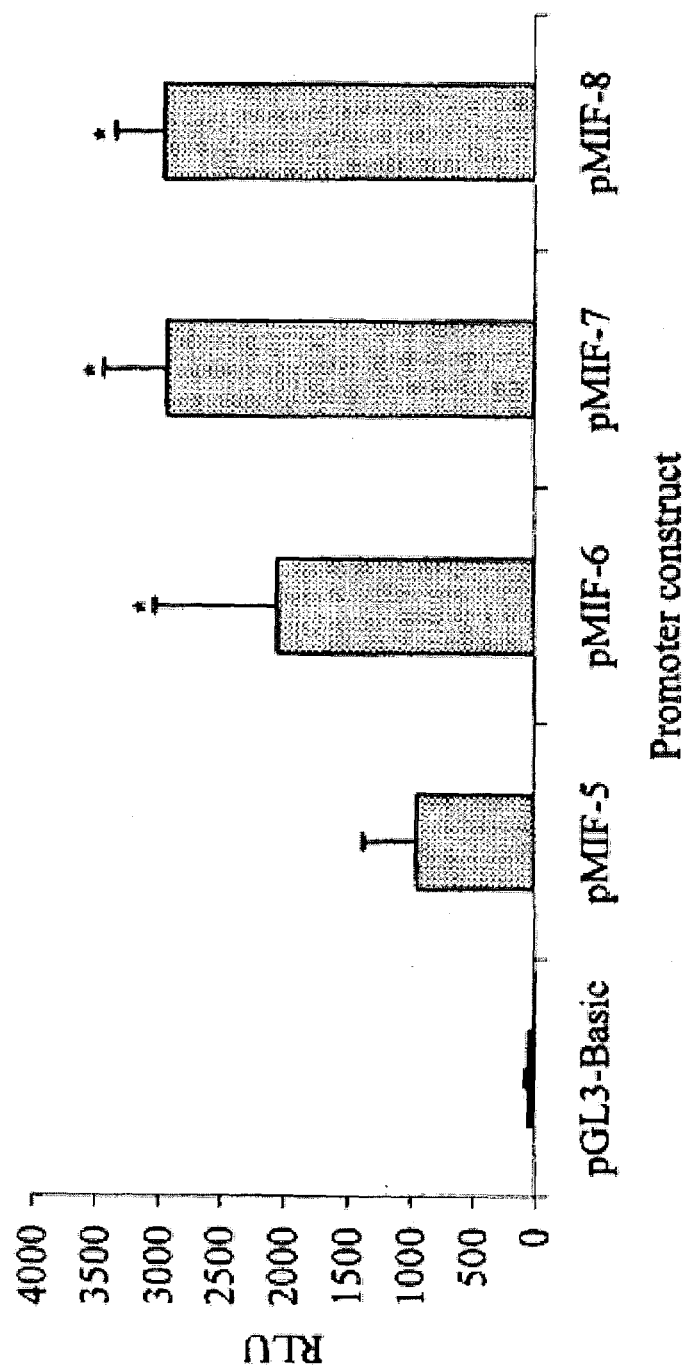
FIG. 2 shows the basal transcriptional activity of human Mif promoter polymorphic variants in Cos-7 cells. MIF promoter activity was determined by dual luciferase assays with results expressed as relative light units (RLU). Cos-7 cells were transiently co-transfected with 800 ng of test DNA vector: pGL3-basic (negative control), pMIF-5, pMIF-6, pMIF-7, or pMIF-8 (5, 6, 7, or 8-CATT repeat polymorphism specific MIF promoter-luciferase constructs) and 200 ng of control pRLTK vector. After 48 hours, the cells were lysed and luciferase activity was determined in relation to renilla activity using a dual luciferase kit (Promega) and a TD 20/20 luminometer. The data represent the mean of four individual experiments each carried out in duplicate ±STDEV. * indicates P<0.03 vs. activity of pMIF-5 construct.
Figure 3:
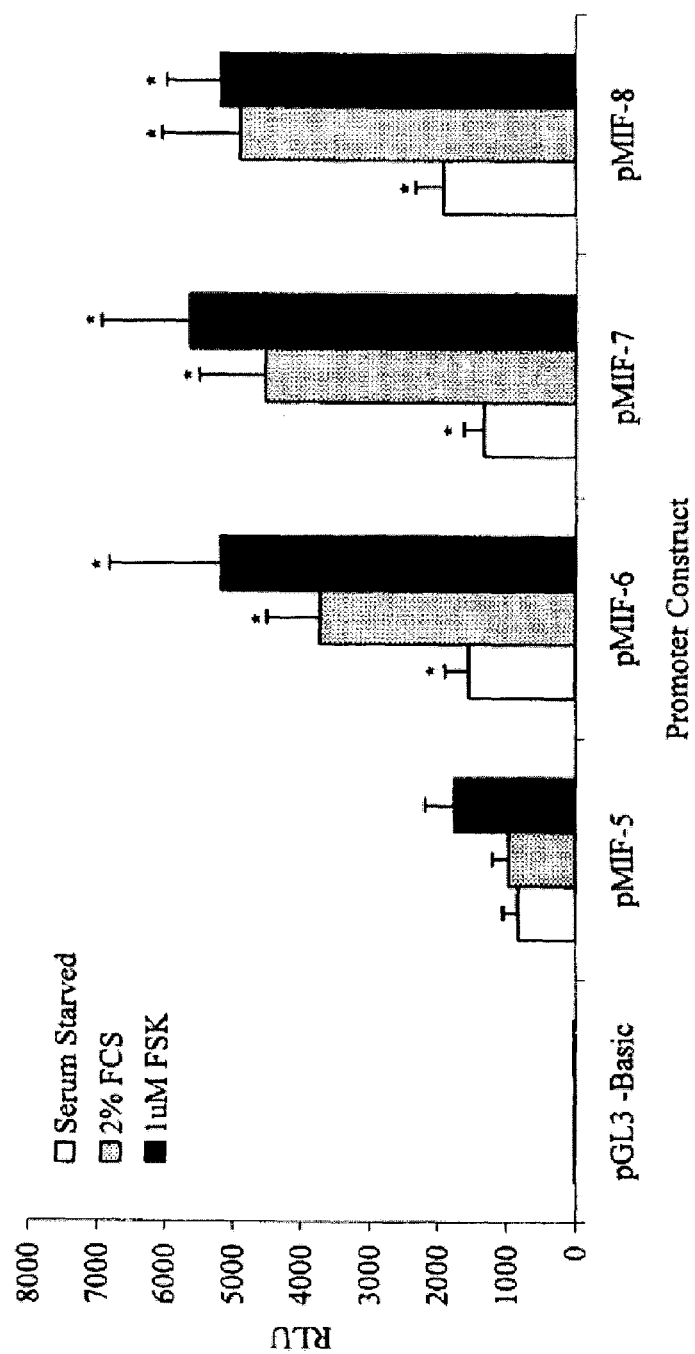
FIG. 3 shows the effect of CATT-repeat polymorphic variation on Mif promoter responses to serum and forskolin stimulation in Cos-7 cells. MIF promoter activity was determined by dual luciferase assays with results expressed as relative light units (RLU). Cos-7 cells were transiently co-transfected with 800 ng of test DNA vector: pGL3-basic (negative control), pMIF-5, pMIF-6, pMIF-7, or pMIF-8 (5, 6, 7, or 8-CATT repeat polymorphism specific MIF promoter—luciferase constructs) and 200 ng of control pRLTK vector. After 24 hours of transfection, the cells were washed in PBS and then cultured in serum free media overnight. The cells were then either left unstimulated (serum starved) or treated with 2% fetal calf serum (FCS) or 1 μM forskolin ("1 uM FSK"). After a further twelve hour incubation luciferase activity was determined as in FIG. 2. The data represent the mean of four individual experiments each carried out in duplicate ±STDEV. * indicates P<0.03 vs. activity of pMIF-5 construct.

Transfection of the Mif promoter-regulated luciferase constructs into Cos-7 cells, A549 cells, and CCD-19Lu cells was associated with strong basal promoter activity, as indicated by high luciferase production, when compared to control vector (pGL3-Basic) (FIG. 2 and data not shown). Promoter activity was increased by forskolin (an inducer of cAMP synthesis 23) and serum stimulation (FIG. 3), as well as phorbol ester stimulation (data not shown). In general, basal promoter activity was high in each of the cell lines tested when compared to negative (empty pGL3 vector) and positive (pRL-TK) controls, and these data appeared to correlate with the high level of endogenous MIF protein expression that was observed in these cell lines (data not shown). Of note, in each of the cell lines tested, the 5-CATT repeat MIF promoter construct showed significantly lower transcriptional activity when compared to the 6, 7, or 8-CATT repeat promoter constructs.

REFERENCE LIST

The following documents are cited parenthetically by number in the specification above.

1. Bucala, "MIF Rediscovered: Cytokine, Pituitary Hormone, and Glucocorticoid-Induced Regulator of the Immune Response", FASEB Journal, 10, 1607–1613 (1996).
2. Leech, et al. "Macrophage Migration Inhibitory Factor in Rheumatoid Arthritis: Evidence of Proinflammatory Function and Regulation by Glucocorticoids", Arthritis Rheum., 42, 1601–1608 (1999).
3. Bernhagen. et al., "MIF is a Pituitary-Derived Cytokine that Potentiates Lethal Endotoxemia", Nature, 365, 756–759 (1993).
4. Bernhagen, et al., "The Emerging Role of MIF in Septic Shock and Infection", Biotherapy, 1995; 8, 123–127 (1995).
5. Donnelly, et al., "Macrophage Migration Inhibitory Factor and Acute Lung Injury", Chest, 1999; 116, 111S (1999).
6. Yang, et al., "Reversal of Established Rat Crescentic Glomerulonephritis by Blockade of Macrophage Migration Inhibitory Factor (MIF): Potential Role of MIF in Regulating Glucocorticold Production", Molecular Medicine, 4, 413–424 (1998).
7. David, "Delayed Hypersensitivity in vitro: Its Mediation by Cell-Free Substances Formed by Lymphoid Cell-Antigen Interaction", Proc Natl Acad Sci USA, 56, 72–77 (1996).
8. Calandra, et al., "Macrophage is an Important and Previously Unrecognized Source of Macrophage-Migration Inhibitory Factor", J. Exp. Med., 179, 1895–1902 (1994).
9. Onodera, et al., "High Expression of Macrophage Migration Inhibitory Factor in the Synovial Tissues of Rheumatoid Joints", Cytokine, 11, 163–167 (1999).
10. Calandra, et al., "Protection from Septic Shock by Neutralization of Macrophage Migration Inhibitory Factor", Nat. Med.; 6, 164–170 (2000).
11. Bacher, et al., "An Essential Regulatory Role for Macrophage Migration Inhibitory Factor in T-cell Activation", Proc. Natl. Acad. Sci. USA, 93, 7849–7854 (1996).
12. Satoskar, et al., "Migration-Inhibitory Factor Gene-Deficient Mice are Susceptible to Cutaneous Leishmania Major Infection", Infect. Immun.; 69, 906-911 (2001).
13. Benigni, et al., "The Proinflammatory Mediator Macrophage Migration Inhibitory Factor Induces Glucose Catabolism in Muscle", J. Clin. Invest., 2000; 106, 1291–1300 (2000).
14. Abe, et al., "Regulation of the CTL Response by Macrophage Migration Inhibitory Factor", J. Immunol.; 166, 747–753 (2001).
15. Benihagen, et al., "Purification and Characterization of the Cytokine Macrophage-Migration Inhibitory Factor (MIF)", FASEB Journal, 8, A1417 (1994).
16. Onodera, et al., "Macrophage Migration Inhibitory Factor Up-Regulates Expression of Matrix Metalloproteinases in Synovial Fibroblasts of Rheumatoid Arthritis", J. Biol. Chem., 275, 444–450 (2000).

17. Meyer-Siegler, et al., "Macrophage Migration Inhibitory Factor Increases MMP-2 Activity in DU-145 Prostate Cells", Cytokine, 12, 914–921 (2000).

18. Mitchell, et al., "Sustained Mitogen-Activated Protein Kinase (MAPK) and Cytoplasmic Phospholipase A2 Activation by Macrophage Migration Inhibitory Factor (MIF). Regulatory Role in Cell Proliferation and Glucocorticoid Action", J. Biol. Chem.; 274, 18100–18106 (1999).

19. Hudson, et al., "A Proinflammatory Cytokine Inhibits p53 Tumor Suppressor Activity", J. Exp. Med., 190: 1375–1382 (1999).

20. Mitchel, et al., "Macrophage Migration Inhibitory Factor (MIF) Sustains Macrophage Proinflammatory Function by Inhibiting p53: Regulatory Role in the Innate Immune Response", Proc. Natl. Acad. Sci. USA, (In press).

21. Alam, et al., "Reporter Genes: Application to the Study of Mammalian Gene Transcription", Anal. Biochem., 188, 245–254 (1990).

22. Naylor, et al., "Reporter Gene Technology: the Future Looks Bright, Biochem. Pharmacol., 58, 749–757 (1999).

23. Seamon, et al., "Forskolin: A Unique Diterpene Activator of Cyclic AMP-Generating Systems", J. Cyclic Nucleotide Res., 7, 201–224 (1981).

24. McGuire, et al., "Variation in the TNF-α Promoter Region Associated with Susceptibility to Cerebral Malaria", Nature, 371, 508–510 (1994).

25. Francis, et al. "Interleukin-I Receptor Antagonist Gene Polymorphism and Coronary Artery Disease", Circulation, 99, 861–866 (1999).

26. Buchs, et al., "IL-I β and IL-I Ra Gene Polymorphisms and Disease Severity in Rheumatoid Arthritis: Interaction with Their Plasma Levels", Genes Immun., 2, 222–228 (2001).

27. Mu, et al., "Tumor Necrosis Factor a Microsatellite Polymorphism is Associated with Rheumatoid Arthritis Severity Through an Interaction with the HLA-DRB1 Shared Epitope", Arthritis Rheum., 42, 438–442 (1999).

28. van Krugten, et al., "Association of the TNF +489 Polymorphism with Susceptibility and Radiographic Damage in Rheumatoid Arthritis", Genes Immun., 1, 91–96 (1999).

29. Sampey, et al., "Regulation of Synoviocyte Phospholipase A2 and Cyclooxygenase 2 by Macrophage Migration Inhibitory Factor", Arthritis Rheum., 44, 1273–1280 (2001).

30. Mikulowska, et al., "Macrophage Migration Inhibitory Factor is Involved in the Pathogenesis of Collagen Type 11-Induced Arthritis in Mice", J. Immunol., 158, 5514–5517 (1997).

31. Leech, et al., "Regulation of Macrophage Migration Inhibitory Factor by Endogenous Glucocorticoids in Rat Adjuvant-Induced Arthritis", Arthritis Rheum., 43, 827–833 (2000).

32. Nimer, et al., "The Repeated Sequence CATT(A/T) is Required for Granulocyte-Macrophage Colony-Stimulating Factor Promoter Activity", Mol. Cell. Biol., 10, 6084–6088 (1990).

33. Nimer, et al., "Adjacent, Cooperative Elements Form a Strong, Constitutive Enhancer in the Human Granulocyte-Macrophage Colony-Stimulating Factor Gene", Blood, 87, 3694–3703 (1996).

34. Ye, et al., "Identification of a DNA Binding Site for the Nuclear Factor YYI in the Human GM-CSF Core Promoter", Nucleic Acids Res., 22, 5672–5678 (1994).

35. Ye, et al., "Characterization of the Human Granulocyte-Macrophage Colony-Stimulating Factor Gene Ppromoter: An AP I Complex and an Spl-Related Complex Transactivate the Promoter Activity that is Suppressed by a YYI Complex", Mol. Cell Biol., 16, 157–167 (1996).

36. Cohen, et al., "Role of Pit-I in the Gene Expression of Growth Hormone, Prolactin, and Thyrotropin", Endocrinol. Metab. Clin. North Am., 25, 523–540 (1996).

37. Calandra, et al., "MIF as a Glucocorticoid-Induced Modulator of Cytokine Production", Nature, 377, 68–71 (1995).

38. Waeber, et al, "Transcriptional Activation of the Macrophage Migration-Inhibitory Factor Gene by the Corticotropin-Releasing Factor is Mediated by the Cyclic Adenosine 3',5'-Monophosphate Responsive Element-Binding Protein CREB in Pituitary Cells", Mol. Endocrinol, 12, 698–705 (1998).

39. Baerwald, et al., "Corticotropin Releasing Hormone (CRH) Promoter Polymorphisms in Various Ethnic Groups of Patients with Rheumatoid Arthritis", Z. Rheumatol., 59, 29–34 (2000).

40. Chikanza, et al., "Defective Hypothalamic Response to Immune and Inflammatory Stimuli in Patients with Rheumatoid Arthritis", Arthritis Rheum., 35, 1281–1288 (1992).

41. Donn, et al., "A Novel 5'-Flanking Region Polymorphism of Macrophage Migration Inhibitory Factor is Associated with Systemic-Onset Juvenile Idiopathic Arthritis", Arthritis Rheum., 44, 1782–1785 (2001).

42. Feldmann, et al., "Anti-TNF Alpha Therapy of Rheumatoid Arthritis: What Have We Learned?", Annu. Rev. Immunol., 19, 163–196 (1901).

43. Calandra, et al., "MIF, a Previously Unrecognized Macrophage Cytokine, Induces Macrophages to Secrete TNF-α and Overcomes Dexamethasone-Suppression of TNF Secretion", Clinical Research, 42, A138 (1994).

44. Paralkar, et al., "Cloning the Human Gene for Macrophage Migration Inhibitory Factor (MIF)", Genomics, 19: 48–51 (1994).

45. Tsuda, et al., "Separation of Nucleotides by High-Voltage Capillary Electrophoresis", J. Appl. Biochem., 5, 330–336 (1983).

All patents, patent applications and publications mentioned hereinabove are hereby incorporated by reference in their entirety.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of detecting a CATT tetranucleotide repeat polymorphism in the promoter of the human macrophage inhibitory factor gene, SEQ ID NO: 12, wherein the CATT tetranucleotide repeat begins at position 259 of SEQ ID NO: 12, comprising:

amplifying the promoter with a PCR primer set,
analyzing the size of the amplified product to determine how many CATT tetranucleotide repeats are present, and
detecting 5, 7 or 8 CATT tetranucleotide repeats.

2. The method of claim 1 wherein said PCR primer set is SEQ ID NO: 1 and SEQ ID NO: 2.

3. The method of claim 1 wherein said PCR primer set is SEQ ID NO: 1 and SEQ ID NO: 9.

* * * * *

UNITED STATES PATENT AND TRADEMARK OFFICE
CERTIFICATE OF CORRECTION

Page 1 of 2

PATENT NO.           : 7,205,107 B2
APPLICATION NO.      : 10/323656
DATED                : April 17, 2007
INVENTOR(S)          : John A. Baugh et al.

It is certified that error appears in the above-identified patent and that said Letters Patent is hereby corrected as shown below:

Drawings:
        Replace Figure 4A with the figure as shown on the attached page.

Signed and Sealed this

Sixteenth Day of October, 2012

David J. Kappos
*Director of the United States Patent and Trademark Office*

FIG. 4A

```
ctgcaggaac caatacccat aggctatttg tataaatggg ccatggggcc tcccagctgg
aggctggctg gtgccacgag ggtcccacag gcatgggtgt ccttcctata tcacatggcc
ttcactgaga ctggtatatg gattgcacct atcagagacc aaggacagga cctccctgga
aatctctgag gacctggcct gtgatccagt tgctgccttg tcctcttcct gctatgtcat
ggcttatctt ctttcaccca ttcattcatt cattcattca ttcagcagta ttagtcaatg
tctcttgata tgcctggcac ctgctagatg gtccccgagt ttaccattag tggaaaagac
atttaagaaa ttcaccaagg gctctatgag aggccataca cggtggacct gactagggtg
tggcttccct gaggagctga agttgcccag aggcccagag aaggggagct gagcacgttt
gaaccactga acctgctctg gacctcgcct ccttccttcg gtgcctccca gcatcctatc
ctctttaaag agcaggggtt cagggaagtt ccctggatgg tgattcgcag gggcagctcc
cctctcacct gccgcatgac tacccgccc catctcaaac acacaagctc acgcatgcgg
gactggagcc cttgaggaca tgtggcccaa agacaggagg tacagggct cagtgcgtgc
agtggaatga actgggcttc atctctggaa gggtaagggg ccatcttccg ggttcaccgc
cgcatcccca cccccggcac agcgcctcct ggcgactaac atcggtgact tagtgaaagg
actaagaaag acccgaggcg aggccggaac aggccgattt ctagccgcca agtggagaac
aggttggagc ggtgcgccgg gcttagcggc ggttgctgga ggaacgggcg gagtcgccca
gggtcctgcc ctgcgggggt cgagccgagg caggcggtga cttccccact cggggcggag
ccgcagcctc gcggggggcgg ggcctggcgc cggcggtggc gtcacaaaag gcgggaccac
agtggtgtcc gagaagtcag gcacgtagct cagcggcggc cgcggcgcgt gcgtctgtgc
ctctgcgcgg gtctcctggt ccttctgcca tcatgccgat gttcatcgta aacaccaacg
tgccccgcgc ctccgtgccg gacgggttcc tctccgagct cacccagcag ctggcgcagg
ccaccggcaa gccccccag gtttgccggg aggggacagg aagaggggg tgcccaccgg
```